(12) United States Patent
Schubert et al.

(10) Patent No.: US 8,313,559 B2
(45) Date of Patent: Nov. 20, 2012

(54) ALUMINUM AMINOCARBOXYLATES AS POROUS METAL ORGANIC FRAMEWORKS

(75) Inventors: Markus Schubert, Ludwigshafen (DE); Ulrich Mueller, Neustadt (DE); Christoph Kiener, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 388 days.

(21) Appl. No.: 12/601,022

(22) PCT Filed: May 20, 2008

(86) PCT No.: PCT/EP2008/056140
§ 371 (c)(1),
(2), (4) Date: Jan. 6, 2010

(87) PCT Pub. No.: WO2008/142059
PCT Pub. Date: Nov. 27, 2008

(65) Prior Publication Data
US 2010/0154635 A1 Jun. 24, 2010

(30) Foreign Application Priority Data
May 21, 2007 (EP) .................................. 07108526

(51) Int. Cl.
B01J 20/28 (2006.01)
B01J 20/30 (2006.01)
F17C 11/00 (2006.01)

(52) U.S. Cl. ............................................. 95/90; 96/108
(58) Field of Classification Search .............. 95/90, 900; 96/108; 206/0.7; 502/400
See application file for complete search history.

(56) References Cited

U.S. PATENT DOCUMENTS

| | | | |
|---|---|---|---|
| 6,930,193 B2 * | 8/2005 | Yaghi et al. ...................... 556/46 |
| 7,556,673 B2 | 7/2009 | Schubert et al. |
| 2008/0121105 A1 | 5/2008 | Schubert et al. |
| 2008/0188677 A1 | 8/2008 | Schubert et al. |
| 2008/0206093 A1 | 8/2008 | Muller et al. |
| 2008/0214806 A1 | 9/2008 | Schubert et al. |
| 2008/0227634 A1 | 9/2008 | Muller et al. |
| 2008/0281116 A1 | 11/2008 | Schubert et al. |
| 2008/0300387 A1 | 12/2008 | Schubert et al. |
| 2009/0032023 A1 | 2/2009 | Pastre et al. |
| 2009/0042000 A1 | 2/2009 | Schubert et al. |
| 2009/0092818 A1 | 4/2009 | Kiener et al. |
| 2009/0133576 A1 | 5/2009 | Schubert et al. |
| 2009/0171107 A1 | 7/2009 | Puetter et al. |
| 2009/0183996 A1 | 7/2009 | Richter et al. |
| 2009/0198079 A1 | 8/2009 | Schubert et al. |
| 2009/0281341 A1 | 11/2009 | Schubert et al. |
| 2010/0166644 A1 * | 7/2010 | Schubert et al. ........... 423/648.1 |

FOREIGN PATENT DOCUMENTS

| | | |
|---|---|---|
| WO | 2007 023134 | 3/2007 |
| WO | 2007 113118 | 10/2007 |
| WO | 2007 131948 | 11/2007 |
| WO | 2008 061958 | 5/2008 |
| WO | 2008 062034 | 5/2008 |
| WO | 2008 129024 | 10/2008 |

OTHER PUBLICATIONS

U.S. Appl. No. 13/002,612, filed Jan. 4, 2011, Leung, et al.
U.S. Appl. No. 13/003,839, filed Jan. 12, 2011, Schubert, et al.
U.S. Appl. No. 12/863,339, filed Jul. 16, 2010, Schubert, et al.
Millward, Andrew R. et al., "Metal-Organic Frameworks with Exceptionally High Capacity for Storage of Carbon Dioxide at Room Temperature", J. Am. Chem. Soc., vol. 127, No. 51, pp. 17998-17999, (Jan. 12, 2005).
Senkovska, Irena et al., "Solvent-Induced Pore-Size Adjustment in the Metal-Organic Framework $[Mg_3(ndc)_3(dmf)_4]$ (ndc = naphthalenedicarboxylate)", Eur. J. Inorg. Chem., vol. 2006, No. 122, pp. 4564-4569, (Sep. 25, 2006).
Loiseau, Thierry et al., "A Rationale for the Large Breathing of the Porous Aluminum Terephthalate (MIL-53) Upon Hydration", Chem. Eur. J., vol. 10, No. 6, pp. 1373-1382, (Mar. 15, 2004).
U.S. Appl. No. 12/063,522, filed Feb. 11, 2008, Schubert, et al.
U.S. Appl. No. 12/161,024, filed Jul. 16, 2008, Schubert, et al.
U.S. Appl. No. 12/294,789, filed Sep. 26, 2008, Schubert.
U.S. Appl. No. 12/375,218, filed Jan. 27, 2009, Schubert, et al.
U.S. Appl. No. 12/447,671, filed Apr. 29, 2009, Schubert, et al.
U.S. Appl. No. 12/516,083, filed May 22, 2009, Muller, et al.
U.S. Appl. No. 12/521,337, filed Jun. 26, 2009, Schubert, et al.

* cited by examiner

*Primary Examiner* — Frank Lawrence, Jr.
(74) *Attorney, Agent, or Firm* — Oblon, Spivak, McClelland, Maier & Neustadt, L.L.P.

(57) ABSTRACT

A porous metal organic framework containing an at least bidentate organic compound coordinated to a metal ion, wherein the metal ion is $Al^{III}$ and the at least bidentate organic compound is 2-aminoterephthalic acid, and wherein the framework is in powder form and has a specific surface area determined by the Langmuir method (N2, 77 K) of at least 2500 m²/g. In addition, a shaped body containing the metal organic framework, processes for preparing the metal organic framework and shaped body, and processes for storing and separating gases with the metal organic framework and shaped body.

20 Claims, 1 Drawing Sheet

ALUMINUM AMINOCARBOXYLATES AS POROUS METAL ORGANIC FRAMEWORKS

The present invention relates to a porous metal organic framework, shaped bodies comprising this and also a process for preparing it and their use.

Porous metal organic frameworks are known from the prior art. They are, in particular, porous and can frequently be employed in applications comparable to those known for inorganic zeolites.

Metal organic frameworks usually comprise an at least bidentate organic compound which is coordinated to a metal ion and together with the metal ion forms the skeleton of the metal organic framework.

The appropriate choice of metal and/or organic compound makes optimization for the desired field of use possible. For example, the choice of organic compound can have an influence on the pore distribution. Furthermore, the metal can make a contribution to adsorption processes.

There is therefore a continual need for specific metal organic frameworks which, in particular, have extraordinary properties attributable to the choice of the metal and of the organic compound.

In addition, it has been found that modification of the processes for preparing metal organic frameworks makes it possible to obtain different frameworks which are nevertheless made up of the same metal and the same organic compound.

Such an example is described in the European patent application number 06123200.5. Here, aluminum naphthalenedicarboxylate was able to be prepared as metal organic framework by altering the reaction conditions so that a new structure was formed. The aluminum naphthalenedicarboxylate known hitherto as metal organic framework had an "MIL-69" structure. A further example is described in the European patent application number 07 106802.7.

Aluminum-based metal organic frameworks are interesting materials since, owing to strong coordinate bonds, comparatively robust metal organic frameworks can be obtained. In addition, the $Al^{3+}$ ion is, owing to its octahedral coordination, suitable in principle for building up three-dimensional framework compounds. Furthermore, the salts of aluminum which can be used as starting material are readily available and inexpensive.

Finally, it is known from the U.S. patent application Ser. No. 11/563,101, filed on Nov. 24, 2006 that a metal organic framework based on aluminum and aminoterephthalic acid likewise has an "MIL-53" structure.

This framework is, in particular, suitable for use as adsorbent, in particular of carbon dioxide.

Despite the metal organic frameworks known from the prior art, there is a continuing need for alternative frameworks which have superior properties, especially in respect of the storage and separation of gases.

In particular, there is likewise a need for alternative processes for preparing novel porous metal organic frameworks based on known metals and organic compounds.

It is therefore an object of the present invention to provide such frameworks and processes.

The object is achieved by a porous metal organic framework comprising an at least bidentate organic compound coordinated to at least one metal ion, where the at least one metal ion is $Al^{III}$ and the at least bidentate organic compound is an at least monoamino-substituted aromatic dicarboxylic acid selected from the group consisting of terephthalic acid, 2,6-naphthalenedicarboxylic acid, 1,4-naphthalenedicarboxylic acid, 1,5-naphthalenedicarboxylic acid and derivatives thereof in which at least one CH group in the ring has been replaced by nitrogen, wherein the framework in powder form has a specific surface area determined by the Langmuir method ($N_2$, 77 K) of at least 2500 $m^2/g$.

The object is additionally achieved by a process for preparing a porous metal organic framework according to the invention, which comprises the step reaction of a reaction mixture comprising an aluminum (III) compound, an at least bidentate organic compound which is an at least monoamino-substituted aromatic dicarboxylic acid selected from the group consisting of terephthalic acid, 2,6-naphthalenedicarboxylic acid, 1,4-naphthalenedicarboxylic acid, 1,5-naphthalene-dicarboxylic acid and derivatives thereof in which at least one CH group in the ring has been replaced by nitrogen or one of its salts and an organic solvent at a temperature in the range from 75° C. to 200° C., with the molar ratio of $Al^{III}$ to the substituted aromatic dicarboxylic acid being less than 1.

Figure 1:
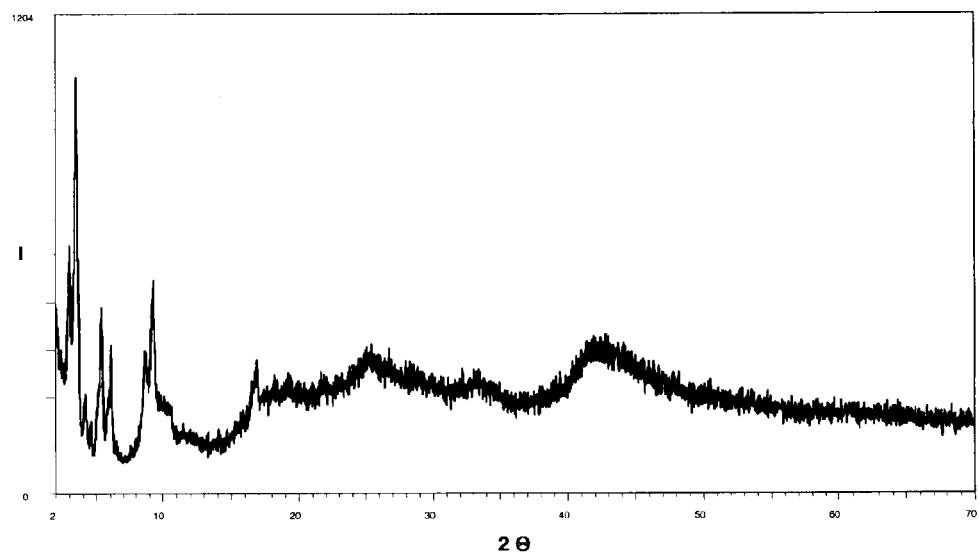
FIG. 1: An X-ray diffraction (XRD) pattern of the Al—($NH_2$)BDC framework of Example 1, which differs significantly from the MIL-53 structure.

It has been found that aromatic dicarboxylic acids which are substituted by at least one amino group together with aluminum form porous metal organic frameworks which have not been described hitherto when the molar ratio of $Al^{III}$ to the substituted aromatic dicarboxylic acid is <1 in the reaction according to the process of the invention. The porous metal organic frameworks obtained in this way have, in powder form, a specific surface area determined by the Langmuir method which is far above the corresponding surface areas of the Al-based frameworks known from the prior art. This is at least 2500 $m^2/g$.

The at least bidentate organic compound comprised in porous metal organic frameworks according to the invention is an at least monoamino-substituted aromatic dicarboxylic acid selected from the group consisting of terephthalic acid, 2,6-naphthalenedicarboxylic acid, 1,4-naphthalenedicarboxylic acid, 1,5-naphthalene-dicarboxylic acid and derivatives thereof in which at least one CH group in the ring has been replaced by nitrogen.

These acids can be present as partially or fully deprotonated carboxylates in the metal organic framework.

Aminoterephthalic acid derivatives in which at least one CH group in the ring has been replaced by N are corresponding pyridines, pyridazines, pyrimidines or 1,2,4-triazines. Derivatives of naphthalenedicarboxylic acids are, in particular, dicarboxylic acids based on isoquinoline, quinoline, phthalazine, 1,8-naphthyridine, quinoxaline, quinazoline, cinnoline and pteridine.

The aromatische dicarboxylic acid can bear one or more, for example two, three or four, amino groups. However, the aromatic dicarboxylic acid is preferably substituted by only one amino group. For the purposes of the present invention, an amino group is the functional group NRR' in which R and R' are each, independently of one another, H, $CH_3$, $C_2H_5$, preferably H.

As substituted aromatic dicarboxylic acids, particular preference is given to terephthalic acid and 2,6-naphthalenedicarboxylic acid, in particular terephthalic acid.

The aromatic dicarboxylic acid is preferably 2-aminoterephthalic acid.

Accordingly, a particularly preferred porous metal organic framework according to the invention is formed by aluminum and 2-aminoterephthalic acid. This has a base reflection range $2°<2\Theta<7°$ in the X-ray diffraction pattern, preferably in the range $2.5°<2\Theta<4°$.

Preference is given to more than 40% of the 10 strongest reflections being located at $2\Theta<10°$, more preferably more than 60%.

The elemental composition of Al 2-aminoterephthalate is preferably less than 12% by weight, more preferably less than 10.5% by weight, in particular from 8.0 to 9.5% by weight, of Al and more than 30% by weight, preferably from 35% by weight to 43% by weight, of C.

For the purposes of the present invention, a base reflection is any reflection in the X-ray diffraction pattern (XRD) which produces the highest peak.

The diffraction pattern can be determined as follows: the sample is installed as power in the sample container of a commercially available instrument (Siemens D-5000 diffractometer or Bruker D8-Advance). Cu—K$\alpha$ radiation with variable primary and secondary orifice plates and a secondary monochromator is used as radiation source. The signal is detected by means of a scintillation counter (Siemens) or Solex semiconductor detector (Bruker). The measurement range for $2\theta$ is typically from 2° to 70°. The angle step is 0.02°, and the measurement time per angle step is typically 2-4 s. In the evaluation, reflections are indicated by a signal strength which is at least 3 times the background noise. The area analysis can be carried out manually by drawing a baseline on the individual reflections. As an alternative, programs such as "Topas-Profile" from Bruker can be used, in which case the fitting to the background is then preferably carried out automatically by means of a 1st order polynomial in the software.

The metal organic framework of the invention can be present in powder form or as agglomerate.

The porous metal organic framework of the invention can be used as such in powder form or is converted into a shaped body.

It is accordingly a further aspect of the present invention that the porous metal organic framework of the invention is present as powder.

A further aspect of the present invention is consequently a shaped body comprising the porous metal organic framework of the invention.

The production of shaped bodies comprising metal organic frameworks is described, for example, in WO-A 03/102000.

Preferred methods of producing shaped bodies are extrusion or tableting. In the production of shaped bodies, the framework can be admixed with further materials such as binders, lubricants or other additives which are added during production. It is likewise conceivable for the framework to have further constituents such as adsorbents such as activated carbon or the like.

The possible geometries of the shaped bodies are subject to essentially no restrictions. Examples of shapes are, inter alia, pellets such as circular pellets, pills, spheres, granules, extrudates such as rods, honeycombs, grids or hollow bodies.

To produce these shaped bodies, all suitable processes are possible in principle. The following procedures are particularly preferred:

kneading/pan milling of the framework either alone or together with at least one binder and/or at least one pasting agent and/or at least one template compound to give a mixture; shaping of the resulting mixture by means of at least one suitable method such as extrusion; optional washing and/or drying and/or calcination of the extrudate; optional finishing treatment.

Tableting together with at least one binder and/or another auxiliary.

Application of the framework to at least one porous or nonporous support material. The material obtained can then be processed further to produce a shaped body by the above-described method.

Application of the framework to at least one optionally porous substrate.

Kneading/pan milling and shaping can be carried out by any suitable method, as described, for example, in Ullmann's Enzyklopädie der Technischen Chemie, 4th edition, volume 2, p. 313 ff. (1972).

Kneading/pan milling and/or shaping can, for example, be carried out by means of a piston press, roller press in the presence or absence of at least one binder material, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or at superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder which can in principle be any chemical compound which ensures a viscosity of the composition to be kneaded and/or shaped which is desired for kneading and/or shaping. Accordingly, binders can, for the purposes of the present invention, be either viscosity-increasing or viscosity-reducing compounds.

Preferred binders are, for example, aluminum oxide or binders comprising aluminum oxide, as described, for example, in WO 94/29408, silicon dioxide, as described, for example, in EP 0 592 050 A1, mixtures of silicon dioxide and aluminum oxide, as described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tributoxytitanate, or, for example, trialkoxytitanates, such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols, amphiphilic substances and/or graphite.

As viscosity-increasing compound, it is possible to use, if appropriate in addition to the abovementioned compounds, for example, an organic compound and/or a hydrophilic polymer such as cellulose or a cellulose derivative such as methylcellulose and/or a polyacrylate and/or a polymethacrylate and/or a polyvinyl alcohol and/or a polyvinyl pyrrolidone and/or a polyisobutene and/or a polytetrahydrofuran and/or a polyethylene oxide.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or in admixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds, e.g. calcium carbonate. Such further additives are described, for instance, in EP 0 389 041 A1, EP 0 200 260 A1 or WO 95/19222.

The order of addition of the additives such as template compound, binder, pasting agent, viscosity-increasing substance in shaping and kneading is in principle not critical.

In a further preferred embodiment, the shaped body obtained after kneading and/or shaping is subjected to at least one drying step which is generally carried out at a temperature in the range from 25 to 500° C., preferably in the range from 50 to 500° C. and particularly preferably in the range from 100 to 350° C. It is likewise possible to carry out drying under reduced pressure or under a protective gas atmosphere or by spray drying.

In a particularly preferred embodiment, at least one of the compounds added as additives is at least partly removed from the shaped body during this drying process.

The metal organic framework of the invention comprises pores, in particular micropores or mesopores. Micropores are defined as pores having a diameter of 2 nm or less and mesopores are defined by a diameter in the range from 2 to 50 nm (Pure & Appl. Chem. 57 (1985) 603-619). The presence of micropores and/or mesopores can be checked by means of sorption measurements which determine the uptake capacity of the metal organic frameworks for nitrogen at 77 Kelvin (Langmuir method) in accordance with DIN 66131 and/or DIN 66134.

The specific surface area, calculated according to the Langmuir model (DIN 66131, 66134), of the metal organic framework of the invention in powder form is preferably at least 2600 $m^2/g$, more preferably at least 2700 $m^2/g$, more preferably at least 2800 $m^2/g$, even more preferably at least 2900 $m^2/g$, more preferably at least 3000 $m^2/g$ and particularly preferably at least 3100 $m^2/g$.

Shaped bodies comprising the metal organic framework of the invention can have a lower specific surface area, but this specific surface area is preferably at least 500 $m^2/g$, more preferably at least 600 $m^2/g$, even more preferably at least 700 $m^2/g$, in particular at least 800 $m^2/g$.

The pore distribution measured using Ar according to the BJH method preferably has a maximum in the range from 20 Å to 50 Å, more preferably from 30 to 45 Å.

The porosity (determined by means of Ar) for all pores having a diameter of <4026.7 Å is preferably in the range from 0.6 to 1.5 ml/g, more preferably from 0.8 to 1.5 ml/g, in particular from 0.9 to 1.2 ml/g.

The aluminum compound can be produced by anodic oxidation of metallic aluminum. In such a case, the porous metal organic framework of the invention is prepared by at least partially electrochemical route. Processes for the electrochemical preparation of porous metal organic frameworks are described in WO-A 2005/049892. The aluminum compound for the porous metal organic framework of the invention can also be produced in this way.

In the electrochemical preparation of the porous metal organic framework of the invention, cathodic redeposition of the aluminum ion is preferably at least partially prevented by means of one of the following measures:

(i) use of an electrolyte which promotes cathodic formation of hydrogen;
(ii) addition of at least one compound which leads to cathodic depolarization;
(iii) use of a cathode having a suitable hydrogen overvoltage.

The process can be carried out in an undivided electrolysis cell. Particularly useful cells are gap cells or stacked plate cells. These can be connected in a bipolar fashion. Suitable reaction media are, for example, methanol, ethanol, dimethylformamide, diethylformamide and mixtures of two or more of these solvents.

Furthermore, an electrolyte salt or a plurality of electrolyte salts can be present in the reaction mixture. Here, the electrolyte salt can have a quaternary ammonium ion as cation component and an alkoxysulfate as anion component. The total solids content should be greater than or equal to 0.5% by weight.

The reaction in the process of the invention for preparing the metal organic framework of the invention can also be carried out by a classical route. Here, the aluminum compound is typically an aluminum salt.

The aluminum salt can be in the form of an alkoxide, acetonate, halide, sulfite, as salt of an organic or inorganic, oxygen-comprising acid or a mixture thereof.

An alkoxide is, for example, a methoxide, ethoxide, n-propoxide, i-propoxide, n-butoxide, i-butoxide, t-butoxide or phenoxide.

An acetonate is, for example, acetylacetonate.

A halide is, for example, chloride, bromide or iodide.

An organic, oxygen-comprising acid is, for example, formic acid, acetic acid, propionic acid or another alkylmonocarboxylic acid.

An inorganic, oxygen-comprising acid is, for example, sulfuric acid, sulfurous acid, phosphoric acid or nitric acid.

More preferred aluminum compounds are inorganic aluminum salts such as aluminum chloride, aluminum bromide, aluminum hydrogensulfate, aluminum dihydrogenphosphate, aluminum monohydrogenphosphate, aluminum phosphate, aluminum nitrate.

The aluminum compound can, if appropriate, comprise water of hydration. Preferred aluminum compounds are the hydrates of the chloride, nitrate or sulfate, in particular that of the chloride.

The reaction in the process of the invention for preparing the porous metal organic framework of the invention is carried out at least in the presence of an organic solvent.

Here, it is possible to use solvothermal conditions. For the purposes of the present invention, the term "thermal" refers to a preparative process in which the reaction to form the porous metal organic framework of the invention is carried out in a pressure vessel which is closed during the reaction and is heated to an elevated temperature so that a pressure is built up within the reaction medium in the pressure vessel as a result of the vapor pressure of the solvent present.

The reaction is preferably not carried out in a water-comprising medium and likewise not under solvothermal conditions.

The reaction in the process of the invention is consequently preferably carried out in the presence of a nonaqueous solvent.

The reaction is preferably carried out at a pressure of not more than 2 bar (absolute). However, the pressure is preferably not more than 1230 mbar (absolute). In particular, the reaction takes place under atmospheric pressure. However, slightly superatmospheric or subatmospheric pressures can occur as a result of the apparatus. For the purposes of the present invention, the term "atmospheric pressure" therefore covers a pressure range given by the actual atmospheric pressure ±150 mbar.

The reaction takes place in a temperature range from 75° C. to 200° C. The temperature is preferably in the range from 80° C. to 150° C., the temperature is more preferably in the range from 85° C. to 135° C.

In the process of the invention, the molar ratio (after complete addition) of $Al^{III}$ to the substituted aromatic dicarboxylic acid is less than 1. This ratio is preferably less than 0.85, in particular less than 0.7.

The Al content of the reaction mixture is preferably less than 0.2 mol/l, more preferably less than 0.16 mol/l, even more preferably less than 0.1 mol/l and in particular less than 0.05 mol/l, based on the total volume of the reaction mixture.

The reaction mixture can also comprise a base. This serves, in particular, to make a carboxylic acid used as at least bidentate organic compound readily soluble. The use of an organic solvent frequently makes it unnecessary to use such a base. Nevertheless, the solvent for the process of the invention can be selected so that it itself has a basic reaction, but this is not absolutely necessary for carrying out the process of the invention.

It is likewise possible to use a base. However, it is preferred that no additional base is used.

Furthermore, it is advantageous for the reaction to take place with stirring, which is also advantageous in the case of a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone, sulfolene or mixtures thereof. Preference is given to solvents having a boiling point of at least 100° C. under normal conditions.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane having from 1 to 200 carbon atoms in which one or more up to all hydrogen atoms can have been replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF, DMAc and mixtures thereof. Particular preference is given to DMF.

The term "nonaqueous" preferably refers to a solvent which has a maximum water content of 10% by weight, more preferably 5% by weight, even more preferably 1% by weight, even more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" refers to both pure solvents and mixtures of different solvents.

Furthermore, the process step of reaction of the at least one metal compound with the at least one at least bidentate organic compound can be followed by a calcination step. The temperature set here is typically above 250° C., preferably in the range from 300 to 400° C.

As a result of the calcination step, the at least bidentate organic compound present in the pores can be removed.

In addition or as an alternative thereto, the at least bidentate organic compound (ligand) can be removed from the pores of the porous metal organic framework by treatment of the framework formed with a nonaqueous solvent. Here, the ligand is removed in a type of "extraction process" and, if appropriate, replaced by a solvent molecule in the framework.

The treatment is preferably carried out for at least 30 minutes and can typically be carried out for up to 7 days. This can occur at room temperature or elevated temperature. It preferably occurs at elevated temperature, for example at least 40° C., preferably 60° C. The extraction more preferably takes place at the boiling point of the solvent used (under reflux).

The treatment can be carried out in a simple vessel by slurrying and stirring the framework. It is also possible to use extraction apparatuses such as Soxhlet apparatuses, in particular industrial extraction apparatuses.

Solvents which can be used are those mentioned above, i.e., for example, $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone or mixtures thereof.

Preference is given to methanol, ethanol, propanol, acetone, MEK and mixtures thereof.

A very particularly preferred extractant is methanol.

The solvent used for the extraction can be identical to or different from that used for the reaction of the at least one metal compound with the at least one at least bidentate organic compound. In the "extraction", it is not absolutely necessary but preferred that the solvent is water-free.

The present invention further provides for the use of a porous metal organic framework according to the invention or a shaped body comprising this for the storage or separation of gases.

The term gas comprises both pure gases and gas mixtures.

Processes for storage by means of metal organic frameworks in general are described in WO-A 2005/003622, WO-A 2003/064030, WO-A 2005/049484, WO-A 2006/089908 and DE-A 10 2005 012 087. The processes described there can also be used for the metal organic framework of the invention.

Processes for separation or purification by means of metal organic frameworks in general are described in EP-A 1 674 555, DE-A 10 2005 000938 and the German patent application number DE-A 10 2005 022 844. The processes described there can also be used for the metal organic framework of the invention.

If the porous metal organic framework of the invention is used for storage, this preferably takes place in a temperature range from −200° C. to +80° C. Greater preference is given to a temperature range from −40° C. to +80° C. Particular preference is given to storage at ambient temperature, e.g. room temperature.

Preferred gases are hydrogen, natural gas, town gas, hydrocarbons, in particular methane, ethane, ethyne, acetylene, propane, n-butane and i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon.

The gas is particularly preferably carbon dioxide which is separated off from a gas mixture comprising carbon dioxide. The gas mixture preferably comprises carbon dioxide together with at least $H_2$, $CH_4$ or carbon monoxide. In particular, the gas mixture comprises carbon dioxide together with carbon monoxide. Very particular preference is given to mixtures comprising at least 10 and not more than 45% by volume of carbon dioxide and at least 30 and not more than 90% by volume of carbon monoxide.

A preferred embodiment is pressure swing adsorption using a plurality of parallel adsorption reactors, with the bed of adsorbent consisting entirely or partly of the material of the invention. For the $CO_2/CO$ separation, the adsorption phase preferably takes place at a $CO_2$ partial pressure of from 0.6 to 3 bar and a temperature of at least 20° C. but not more than 70° C. To desorb the adsorbed carbon dioxide, the total pressure in the adsorption reactor concerned is usually reduced to values in the range from 100 mbar to 1 bar.

Preference is also given to the use of the framework of the invention for the storage of a gas at a minimum pressure of 100 bar (absolute). The minimum pressure is more preferably 200 bar (absolute), in particular 300 bar (absolute). Here, the gas is particularly preferably hydrogen or methane. In particular, appropriate pressures for $H_2$ are up to 350 bar (absolute), also up to 700 bar (absolute).

EXAMPLES

Example 1

Preparation of an Al—($NH_2$)BDC Framework According to the Invention 5.89 g of aminoterephthalic acid and 4.62 g of $AlCl_3 \cdot 6H_2O$ are suspended in 250 ml of DMF in a glass flask ($n(Al^{3+})$: n(aminoterephthalic acid)=0.59), heated to 130° C. while stirring and maintained under these conditions for 24 hours. The yellow precipitate formed after about 1 hour is filtered off and washed with 2×100 ml of DMF and 3×100 ml of methanol. The filter cake is subsequently dried at 100° C. for 16 hours in a drying oven (yield: 8.8 g).

The X-ray diffraction pattern (XRD) is shown in FIG. 1 and differs significantly from the MIL-53 structure. In FIG. 1, the intensity I (Lin(Counts)) is shown as a function of the 2 theta scale (2Θ).

The strongest reflections with the base reflection are observed at an angle (2Θ) of 3-4°. The surface area determined using $N_2$ (Langmuir method) is 2888 $m^2/g$.

Example 2

Preparation of an Al—($NH_2$)BDC Framework According to the Invention 23.56 g of aminoterephthalic acid and 18.48 g of $AlCl_3 \cdot 6H_2O$ are suspended in 500 ml of DMF in a glass flask ($n(Al^{3+})$: n(aminoterephthalic acid)=0.59), heated to 130° C. while stirring and maintained under these conditions for 48 hours. The yellow precipitate formed after about 1 hour is filtered off and washed with 2×200 ml of DMF and 3×200 ml of methanol. The filter cake is subsequently dried at 100° C. for 16 hours in a drying oven (yield: 22.0 g).

The XRD is the same as that in Example 1 and differs significantly from the MIL-53 structure: the strongest reflections with the base reflection are observed at an angle (2Θ) of 3-4°.

The surface area determined using $N_2$ (Langmuir method) is 3472 $m^2/g$.

Elemental analysis indicates the following composition: Al 8.8% by weight, H 4.7% by weight, C 37.9% by weight and 5.0% by weight of N. In addition, 2.3% by weight of Cl were found; these can be attributed to remaining impurities from the synthesis mixture. The balance is oxygen.

Comparative Example 3

Preparation of an Al—($NH_2$)BDC MOF Having the MIL-53 Structure 5.89 g of aminoterephthalic acid and 15.8 g of $AlCl_3 \cdot 6H_2O$ are suspended in 250 ml of DMF in a glass flask ($Al^{3+}$: aminoterephthalic acid=2.01), heated to 130° C. while stirring and maintained under these conditions for 24 hours. The yellow precipitate formed after about 1 hour is filtered off and washed with 2×100 ml of DMF and 3×100 ml of methanol. The filter cake is subsequently dried at 100° C. for 16 hours in a drying oven (yield: 8.8 g).

The moderately crystalline substance can be identified as the MIL-53 structure having slightly altered lattice constants by means of the XRD.

The surface area determined using $N_2$ (Langmuir method) is only 961 $m^2/g$.

Elemental analysis indicates the following composition: Al 14.0% by weight, H 3.8% by weight, C 29.7% by weight and 4.7% by weight of N. In addition, 1.3% by weight of Cl were found; these can be attributed to remaining impurities from the synthesis mixture. The balance is oxygen. The Al:C ratio in this structure is significantly different from Example 2.

Comparative Example 4

Preparation of an Al—($NH_2$)BDC MOF Having the MIL-53 Structure 17.7 g of aminoterephthalic acid and 13.8 g of $AlCl_3 \cdot 6H_2O$ are suspended in 250 ml of DMF in a glass flask (Al content of the synthesis mixture: 0.23 mol/l), heated to 130° C. while stirring and maintained under these conditions for 3 hours. The yellow precipitate formed after about 1 hour is filtered off and washed with 2×100 ml of DMF and 3×100 ml of methanol. The filter cake is subsequently dried at 100° C. for 16 hours in a drying oven (yield: 7.9 g).

Figure 2:
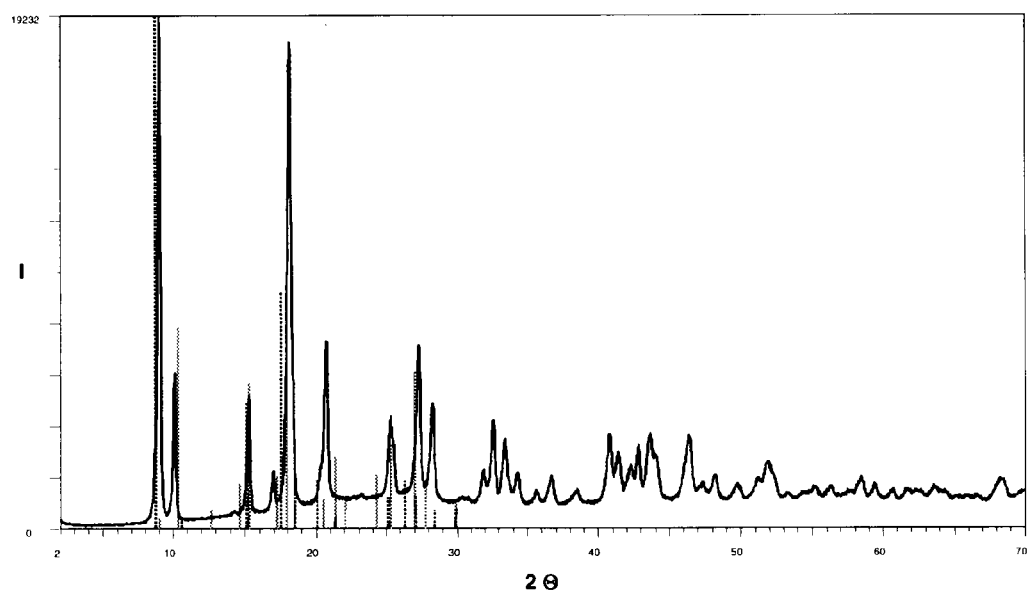
FIG. 2: An XRD pattern of the Al—($NH_2$)BDC framework of Comparative Example 4, which shows the well-crystallized substance has the MIL-53 structure.

The well-crystallized substance can be identified as the MIL-53 structure having slightly altered lattice constants by means of the XRD (FIG. 2). The surface area determined using $N_2$ (Langmuir method) is only 36 $m^2/g$.

Here, FIG. 2 also shows the intensity I (Lin(Counts)) as a function of the 2 theta scale (2Θ).

The invention claimed is:
1. A porous metal organic framework, comprising an at least bidentate organic compound coordinated to a metal ion, wherein the metal ion is $Al^{III}$ and the at least bidentate organic compound is 2-aminoterephthalic acid, and wherein the framework is in powder form and has a specific surface area determined by the Langmuir method ($N_2$, 77 K) of at least 2500 $m^2/g$.

2. The framework according to claim 1, wherein a base reflection in the X-ray diffraction pattern is in the range $2°<2\Theta<7°$.

3. A shaped body, comprising:
a metal organic framework according to claim 1.

4. A process for preparing a porous metal organic framework according to claim 1, the process comprising:
reacting a reaction mixture comprising an aluminum(III) compound, 2-aminoterephthalic acid or a salt thereof, and an organic solvent at a temperature in the range from 75° C. to 200° C., wherein a molar ratio of $Al^{III}$ to the 2-aminoterephthalic acid is less than 1.

5. The process according to claim 4, wherein the organic solvent is N,N-dimethylformamide, N,N-diethylformamide, N,N-dimethylacetamide, or a mixture thereof.

6. A process for storing a gas, the process comprising:
storing the gas in the shaped body according to claim 3.

7. A process for separating gases, the process comprising:
separating the gases with the metal organic framework according to claim 1.

8. The framework according to claim 1, wherein a base reflection in the X-ray diffraction pattern is in the range $2.5°<2\Theta<4°$.

9. The framework according to claim 1, having an Al content of less than 12% by weight and a C content greater than 30% by weight, based on a total weight of the framework.

10. The framework according to claim 1, having an Al content of less than 10.5% by weight and a C content in a range from 35 to 43% by weight, based on a total weight of the framework.

11. The framework according to claim 10, having an Al content in a range from 8.0 to 9.5% by weight, based on the total weight of the framework.

12. The framework according to claim 1, wherein the framework has a specific surface area determined by the Langmuir method ($N_2$, 77 K) of at least 2800 $m^2$/g.

13. The framework according to claim 1, wherein the framework has a specific surface area determined by the Langmuir method ($N_2$, 77 K) of at least 3100 $m^2$/g.

14. The process according to claim 4, wherein the organic solvent is N,N-dimethylformamide.

15. The process according to claim 4, wherein the organic solvent is N,N-diethylformamide.

16. The process according to claim 4, wherein the organic solvent is N,N-dimethylacetamide.

17. The process according to claim 4, wherein a molar ratio of $Al^{III}$ to the 2-aminoterephthalic acid is less than 0.85.

18. The process according to claim 4, wherein a molar ratio of $Al^{III}$ to the 2-aminoterephthalic acid is less than 0.7.

19. The process according to claim 4, wherein the aluminum (III) compound is aluminum chloride, aluminum bromide, aluminum hydrogensulfate, aluminum dihydrogenphosphate, aluminum monohydrogenphosphate, aluminum phosphate, or aluminum nitrate.

20. The process according to claim 4, wherein the aluminum (III) compound is a hydrate of aluminum chloride, aluminum nitrate, or aluminum sulfate.

* * * * *